United States Patent
Peng et al.

(10) Patent No.: US 11,894,125 B2
(45) Date of Patent: Feb. 6, 2024

(54) PROCESSING FUNDUS CAMERA IMAGES USING MACHINE LEARNING MODELS TRAINED USING OTHER MODALITIES

(71) Applicant: GOOGLE LLC, Mountain View, CA (US)

(72) Inventors: Lily Hao Yi Peng, Mountain View, CA (US); Dale R. Webster, San Mateo, CA (US); Avinash Vaidyanathan Varadarajan, Los Altos, CA (US); Pinal Bavishi, Mountain View, CA (US)

(73) Assignee: Google LLC, Mountain View, CA (US)

( * ) Notice: Subject to any disclaimer, the term of this patent is extended or adjusted under 35 U.S.C. 154(b) by 394 days.

(21) Appl. No.: 17/286,392

(22) PCT Filed: Oct. 17, 2018

(86) PCT No.: PCT/US2018/056347
§ 371 (c)(1),
(2) Date: Apr. 16, 2021

(87) PCT Pub. No.: WO2020/081075
PCT Pub. Date: Apr. 23, 2020

(65) Prior Publication Data
US 2021/0357696 A1 Nov. 18, 2021

(51) Int. Cl.
*G16H 30/40* (2018.01)
*G16H 50/20* (2018.01)
(Continued)

(52) U.S. Cl.
CPC ......... *G16H 30/40* (2018.01); *G06F 18/2148* (2023.01); *G06T 7/0012* (2013.01);
(Continued)

(58) Field of Classification Search
CPC ........ G16H 30/40; G16H 50/20; G16H 50/30; G16H 50/70; G16H 30/20; G06F 18/2148;
(Continued)

(56) References Cited

U.S. PATENT DOCUMENTS 5,633,694 A * 5/1997 Mihashi ................. A61B 3/145
351/205
8,885,901 B1 11/2014 Solanki et al.
(Continued)

FOREIGN PATENT DOCUMENTS

CN 107945870 A 4/2018
CN 108231194 A 6/2018
(Continued)

OTHER PUBLICATIONS

Office Action in Indian Appln. No. 202147017022, dated Jan. 12, 2023, 10 pages (with English Translation).
(Continued)

*Primary Examiner* — Santiago Garcia
(74) *Attorney, Agent, or Firm* — Fish & Richardson P.C.

(57) ABSTRACT

Methods, systems, and apparatus, including computer programs encoded on computer storage media, for training a fundus image processing machine learning models that is configured to process one or more fundus images captured by a fundus camera to generate a predicted label. One of the methods includes generating training data, comprising: receiving sets of one or more training fundus images captured by a fundus camera; receiving, for each of the sets, a ground truth label assigned to a different image of the eye of the patient corresponding to the set that has been captured using a different imaging modality; and generating, for each set of training fundus images, a training example that includes the set of training fundus images in association with
(Continued)

the ground truth label assigned to the different image of the patients eye; and training the machine learning model on the training examples in the training data.

20 Claims, 14 Drawing Sheets

(51) Int. Cl.
*G06T 7/00* (2017.01)
*G06F 18/214* (2023.01)

(52) U.S. Cl.
CPC ......... *G16H 50/20* (2018.01); *G06T 2200/04* (2013.01); *G06T 2207/10101* (2013.01); *G06T 2207/20081* (2013.01); *G06T 2207/20084* (2013.01); *G06T 2207/30041* (2013.01)

(58) Field of Classification Search
CPC .............. G06T 7/0012; G06T 2200/04; G06T 2207/10101; G06T 2207/20081; G06T 2207/20084; G06T 2207/30041
See application file for complete search history.

(56) References Cited

U.S. PATENT DOCUMENTS

| | | | |
|---|---|---|---|
| 10,810,512 B1* | 10/2020 | Wubbels | G06N 20/00 |
| 2007/0287932 A1 | 12/2007 | Huang et al. | |
| 2008/0097548 A1* | 4/2008 | Greenberg | A61N 1/3787 607/54 |
| 2011/0091083 A1* | 4/2011 | Liu | G06T 7/0012 382/128 |
| 2012/0083667 A1 | 4/2012 | Isogai et al. | |
| 2012/0213423 A1* | 8/2012 | Xu | G06V 40/193 382/131 |
| 2015/0251771 A1 | 9/2015 | Whitlow et al. | |
| 2016/0235373 A1* | 8/2016 | Sharma | G16H 50/30 |
| 2016/0242638 A1 | 8/2016 | Durbin et al. | |
| 2017/0156582 A1 | 6/2017 | Ehlers et al. | |
| 2017/0286622 A1 | 10/2017 | Cox et al. | |
| 2017/0357879 A1 | 12/2017 | Odaibo et al. | |
| 2018/0084988 A1 | 3/2018 | Chakravorty et al. | |
| 2018/0235467 A1* | 8/2018 | Celenk | A61B 3/14 |
| 2018/0247153 A1 | 8/2018 | Ganapati et al. | |
| 2019/0088359 A1* | 3/2019 | Moore | G06F 16/5838 |
| 2019/0180441 A1* | 6/2019 | Peng | G06T 7/0016 |
| 2020/0202527 A1* | 6/2020 | Choi | G06V 10/82 |
| 2020/0242763 A1* | 7/2020 | Bhuiyan | G06T 7/38 |
| 2020/0345284 A1* | 11/2020 | Tao | A61B 3/12 |
| 2022/0240779 A1* | 8/2022 | Peyman | A61B 5/1176 |

FOREIGN PATENT DOCUMENTS

| | | |
|---|---|---|
| CN | 108351685 A | 7/2018 |
| EP | 1877980 A2 | 1/2008 |
| WO | WO 2006069379 A2 | 6/2006 |
| WO | WO 2009067317 A2 | 5/2009 |
| WO | WO 2017031099 A1 | 2/2017 |
| WO | WO 2018045363 A1 | 3/2018 |
| WO | WO 2018/069768 | 4/2018 |
| WO | WO 2018069768 A2 | 4/2018 |

OTHER PUBLICATIONS

Gulshan et al, "Development and Validation of a Deep Learning Algorithm for Detection of Diabetic Retinopathy in Retinal Fundus Photographs" JAMA the journal of the american medical association, Nov. 2016, 9 pages.
PCT International Preliminary Report on Patentability in International Application No. PCT/US2018/056347, dated Apr. 29, 2021, 14 pages.
PCT International Search Report and Written Opinion in International Appln. PCT/US2018/056347, dated Jul. 9, 2019, 21 pages.
Szegedy et al. "Inception—v4, Inception—ResNet and the Impact of Residual Connections on Learning," arXiv, Aug. 2016, 12 pages.
Venugopalan et al. "Sequence to sequence-video to text." Proceedings of the IEEE International Conference on Computer Vision, 2015, 9 pages.
Xu et al., "Show, attend and tell: Neural image caption generation with visual attention," International conference on machine learning, Jun. 2015, 10 pages.
Yue-Hei Ng et al. "Beyond short snippets: Deep networks for video classification," Proceedings of the IEEE Conference on Computer Vision and Pattern Recognition, 2015, 9 pages.
Ge, "Basic Tutorial on Cardiovascular Impact," Beijing: People's Military Medical Press, Oct. 31, 2011, p. 92.
Mao et al., "Application of binocular indirect opthalmoscopy imaging system in screening training for retinopathy of prematurity," Int J Ophthalmol, Jul. 2011, 11(7):1191-1193.
Office Action in Chinese Appln. No. 201880098753.7, dated Sep. 1, 2023, 24 pages (with English Translation).
Strain et al., "Considerations for management of patients with diabetic macular edema: Optimizing treatment outcomes and minimizing safety concerns through interdisciplinary collaboration," Diabetes Research and Clinical Practice, 2017, pp. 1-9.

* cited by examiner

PROCESSING FUNDUS CAMERA IMAGES USING MACHINE LEARNING MODELS TRAINED USING OTHER MODALITIES

CROSS-REFERENCE TO RELATED APPLICATIONS

This application is a national phase entry under 35 U.S.C. 371 of PCT Application Serial No. PCT/US2018/056347 filed Oct. 17, 2018.

BACKGROUND

This specification relates to processing images using a machine learning model.

Machine learning models receive an input and generate an output, e.g., a predicted output, based on the received input. Some machine learning models are parametric models and generate the output based on the received input and on values of the parameters of the model.

Some machine learning models are deep models that employ multiple layers of models to generate an output for a received input. For example, a deep neural network is a deep machine learning model that includes an output layer and one or more hidden layers that each apply a non-linear transformation to a received input to generate an output.

Some neural networks are recurrent neural networks. A recurrent neural network is a neural network that receives an input sequence and generates an output sequence from the input sequence. In particular, a recurrent neural network uses some or all of the internal state of the network after processing a previous input in the input sequence in generating an output from the current input in the input sequence.

SUMMARY

This specification generally describes a system that generates health analysis data for a patient by processing data that includes one or more fundus images of the patient taken using a fundus camera using a fundus image processing machine learning model.

Particular embodiments of the subject matter described in this specification can be implemented so as to realize one or more of the following advantages.

A health analysis system can effectively train a machine learning model to accurately make a prediction relevant to some aspect of the health of a patient using only one or more images of the retina of the patient's eye captured by a fundus camera. In particular, the system can train the model using labels that are assigned to images captured by a different modality. This different modality can be significantly different from the fundus camera, e.g., a three-dimensional imaging modality like Optical Coherence Tomography (OCT) or a modality that uses radiography to capture eye images. In particular, the different modality generates images that are generally more informative to an expert human user than those generated by the fundus camera but has drawbacks that prevent it from being widely available at screening sites. In other words, fundus cameras are relatively cheap to manufacture, purchase, and maintain and easy to use. The other imaging modality, on the other hand can (i) be more expensive than a typical fundus camera, (ii) have a more complicated workflow to operate than a typical fundus camera (iii) be less readily available at testing locations that a typical fundus camera, and/or (iv) be more harmful to the patient than taking a fundus image with a fundus camera. Thus, while fundus cameras can be readily deployed to screening sites, even in particularly remote or resource-constrained locations, the other imaging modality is generally unavailable at the majority of screening sites. By training the machine learning model using labels assigned to images captured using these other modalities, the trained model can generate highly-accurate predicted labels even though only images captured by the fundus camera are available after training, i.e., no images captured using the other modality are available. Thus, after training, the model can be deployed at screening sites to make highly-accurate predictions without incurring the expense, complicated workflow, potential patient harm, or other factors that are associated with the other modality.

In particular, a fundus image processing machine learning model trained using the techniques described in this specification can generate predicted labels that are not only more accurate than labels predicted by models generated using previously known techniques (i.e., models that were trained on labels assigned to fundus camera images) but also more accurate than those generated by human experts from the same fundus images that are processed by the model. Thus, the machine learning model learns from the labels assigned to the other imaging modality characteristics that were previously thought to only be able to be discerned from the images of the other modality.

An example of the accuracy levels attained by the described models when predicting DME using labels assigned to OCT images can be seen in the results shown in Table 1 below. Table 1 shows the performance levels of a model trained using the described training techniques (OCT model), a model trained using the previously known training techniques (HE model), and three human experts (Specialist 1, Specialist 2, and Specialist 3, three trained retina specialists). In particular, the results shown in Table 1 for the two models were calculated on an entire clinical validation set (of 1033 model inputs), while for the retina specialists the results were calculated only on the images that they marked as gradable. As can be seen from Table 1, the performance of the OCT model far exceeds that of the human experts and the previously known model on a variety of metrics (positive predictive value, negative predictive value, sensitivity, and specificity) despite both models and the human experts having available only fundus camera images as input (or, in the case of the human experts, a source of analysis).

TABLE 1

CI = confidence interval

| Metric | OCT model | HE Model | Specialist 1 | Specialist 2 | Specialist 3 |
| --- | --- | --- | --- | --- | --- |
| Positive Predictive Value (%), 95% CI | 61% [56%-66%] n = 1033 | 39% [36%-43%] n = 1033 | 37% [33%-40%] n = 1004 | 36% [33%-40%] n = 987 | 38% [34%-42%] n = 1001 |
| Negative Predictive Value (%), 95% CI | 93% [91%-95%] | 90% [87%-93%] n = 1033 | 88% [85%-91%] n = 1004 | 89% [85%-92%] n = 987 | 88% [84%-91%] n = 1001 |

TABLE 1-continued

CI = confidence interval

| Metric | OCT model | HE Model | Specialist 1 | Specialist 2 | Specialist 3 |
|---|---|---|---|---|---|
| | n = 1033 | | | | |
| Sensitivity (%), 95% CI | 85% [80%-89%] | 84% [79%-88%] | 84% [80%-89%] | 85% [80%-89%] | 82% [77%-86%] |
| | n = 1033 | n = 1033 | n = 1004 | n = 987 | n = 1001 |
| Specificity (%), 95% CI | 80% [77%-82%] | 52% [48%-55%] | 45% [41%-48%] | 45% [41%-48%] | 50% [47%-54%] |
| | n = 1033 | n = 1033 | n = 1004 | n = 987 | n = 1001 |

The details of one or more embodiments of the subject matter of this specification are set forth in the accompanying drawings and the description below. Other features, aspects, and advantages of the subject matter will become apparent from the description, the drawings, and the claims.

BRIEF DESCRIPTION OF THE DRAWINGS

Like reference numbers and designations in the various drawings indicate like elements.

DETAILED DESCRIPTION

This specification generally describes a system that can generate health analysis data for a patient from an input that includes one or more fundus images of the patient's eye captured using a fundus camera. A fundus image is a photograph of the fundus of one of the eyes of the patient. The fundus of an eye is the interior surface of the eye opposite the lens and includes, among other things, the retina and the optic disc.

Generally, to generate the health analysis data for a given patient, the system processes the one or more fundus images using a fundus image processing machine learning model to generate a predicted label for the patient and then generates the health analysis data from the predicted label. As will be described in more detail below, the predicted label is a prediction that characterizes the health of the patient.

In particular, the system trains the fundus image processing machine learning model on training data that includes labeled training fundus images. That is, the training data includes multiple sets of one or more training fundus image and each set is associated with a ground truth label that identifies the predicted label that the machine learning model should generate for the set of training fundus images. Advantageously, the system leverages a different imaging modality when assigning ground truth labels to training fundus images. For example, the system can assign labels to training fundus images that are generated from optical coherence tomography (OCT) exams.

After the model is trained, i.e., at inference time, the model can be used on images from a fundus camera to generate high-quality predicted labels even though images from the other imaging modality are not available at inference time.

Figure 1A:
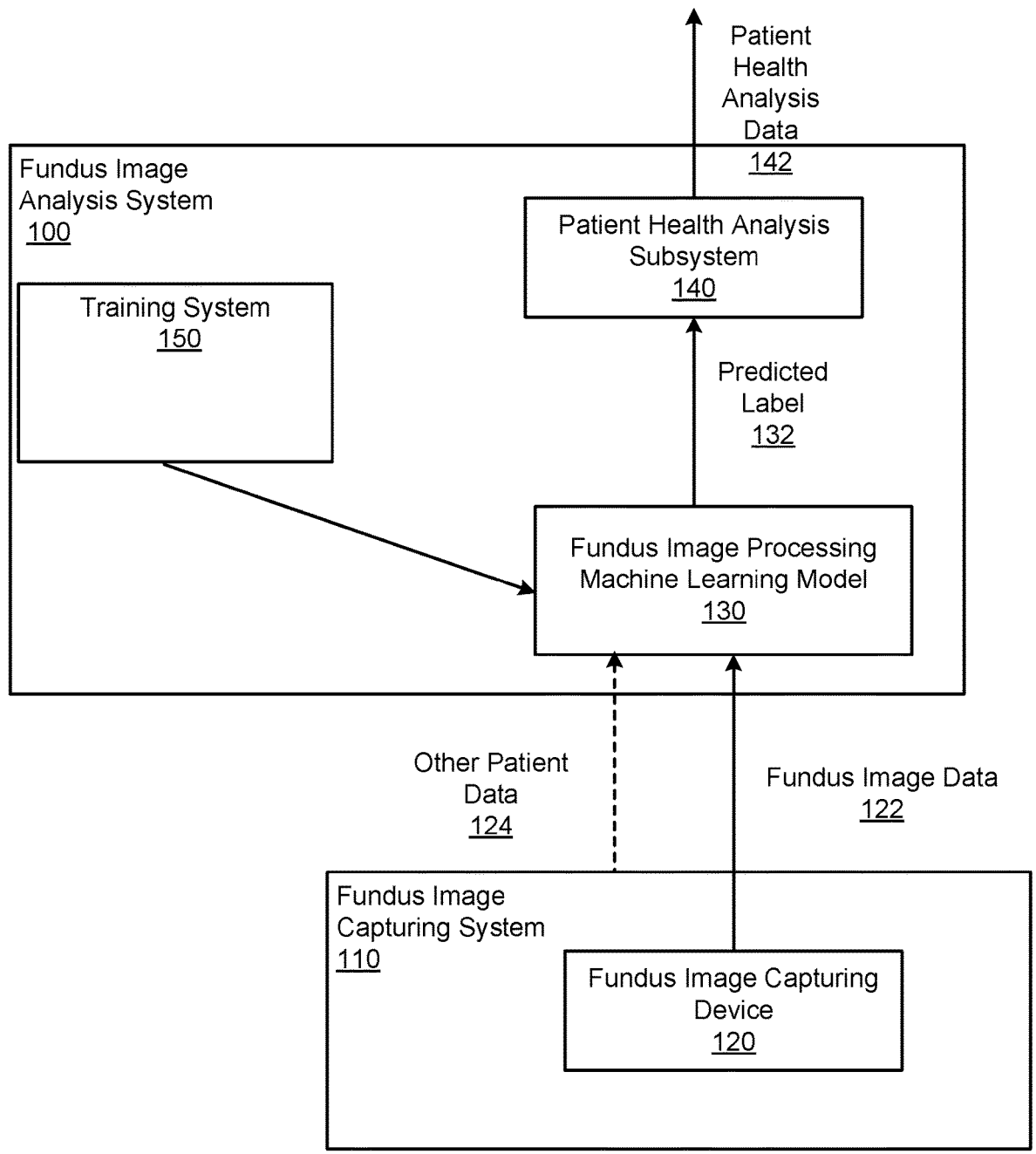
FIG. 1A shows an example fundus image analysis system.

FIG. 1A shows an example fundus image analysis system 100. The fundus image analysis system 100 is an example of a system implemented as computer programs on one or more computers in one or more locations, in which the systems, components, and techniques described below can be implemented.

For a given patient, the fundus image analysis system 100 receives fundus image data 122 that includes one or more fundus images of the patient's eye and generates health analysis data 142 that characterizes the health of the patient.

In some implementations, the fundus image analysis system 100 includes or is in communication with a fundus image capturing system 110 that generates the fundus images and provides them as input fundus image data 122 to the fundus image analysis system. In particular, the fundus image capturing system 110 includes one or more image capturing devices, e.g., an image capturing device 120, that are configured to capture images of the fundus of a patient. Generally, the image capturing device 120 is a specialized fundus camera that is configured to capture an appropriate type of fundus image, e.g., using color fundus photography, stereoscopic photography, wide field or ultra wide field photography, or scanning laser ophthalmoscopy (SLO). A fundus camera generally includes a microscope attached to a camera that captures an appropriate type of image, e.g., using color fundus photography, stereoscopic photography, wide field or ultra wide field photography, or SLO. Such a simple arrangement allows fundus images of a patient's fundus to be captured in a relatively uncomplicated manner. In some cases, the image capturing system 110 includes multiple image capturing devices that capture different types of fundus images.

In other implementations, the fundus image analysis system 100 receives the input fundus image data 122 from an external system, e.g., over a data communication network.

The fundus image analysis system 100 processes the input fundus image data 122 and, optionally, other data for the given patient using a fundus image processing machine learning model 130. The fundus image processing machine learning model 130 is a machine learning model that is configured to process the input fundus image data 122 and, optionally, other patient data 124 to generate a predicted label 132 that characterizes the health of the patient.

How many fundus images are in the fundus image data 122, whether the system 100 receives other patient data 124 and, if so, the nature of the other patient data 124 that is received, and the makeup of the predicted label 132 are dependent on the configuration of the fundus image processing machine learning model 130. Fundus image data, example configurations of the machine learning model 130, and example makeups of the predicted label 132 are described in more detail below with reference to FIGS. 2-9.

The fundus image analysis system 100 also includes a patient health analysis subsystem 140 that receives the predicted label 132 and generates the patient health analysis data 142. Generally, the patient health analysis subsystem 140 generates health analysis data that characterizes the predicted label in a way that can be presented to a user of the system. The patient health analysis subsystem 140 can then provide the health analysis data 142 for presentation to the user in a user interface, e.g., on a user computer of the patient or on a computer of a medical professional, store the health analysis data 142 for future use, or provide the health analysis data 142 for use for some other immediate purpose.

In some implementations, the fundus image analysis system 100 receives requests for patient health analysis data 142 from remote users of user computers over a data communication network. For example, a user computer, e.g., a computer on which the fundus image capturing system 110 is implemented, may be able to submit a request to the fundus image analysis system 100 over the data communication network by providing fundus image data as part of making an Application Programming Interface (API) call to the fundus image analysis system 100. In response to the API call, the fundus image analysis system 100 can generate the health analysis data 142 and transmit the health analysis data to the user computer over the data communication network.

Additionally, in some implementations, the machine learning model 130 is implemented by one or more computers that are remote from the fundus image analysis system 100. In these implementations, the fundus image analysis system 100 can access the machine learning model 130 by making an API call over a network that includes the input to the machine learning model 130 and can receive the predicted label 132 in response to the API call.

While the description in this specification generally describes a single machine learning model 130 that generates a particular predicted label, in some cases the system 100 includes or communicates with an ensemble of multiple machine learning models for a given kind of predicted label. Each machine learning model 130 generates the same kind of predicted label, and the system 100 or another system can combine the predicted labels generated by the ensemble, e.g., by computing a measure of central tendency, e.g., mean, median, minimum, or maximum, of the predicted labels. The combined output can then be treated as the predicted label 132 by the system 100.

The fundus image analysis system 100 also includes a training system 150 that trains the machine learning model 130 to generate predicted labels, i.e., trains the machine learning model to adjust the values of the parameters of the model to improve the accuracy of the predictions made by the model. Once the model 130 has been trained, the fundus image analysis system 100 can use the trained values of the model parameters to make predictions for new patients.

In particular, the training system 150 trains the fundus image processing machine learning model 130 on training data that includes labeled training fundus images. That is, each training fundus image in the training data is associated with a ground truth label that identifies the predicted label that the machine learning model should generate for the training fundus image. Advantageously, the system leverages a different imaging modality when assigning ground truth labels to training fundus images. As will be described in more detail below with reference to FIG. 1B, the system obtains ground truth labels assigned to images of a patient's eye captured using the different imaging modality and associates those labels with the corresponding training fundus images captured using a fundus camera. Because of this, after training, the model exhibits performance that is much improved relative to a model trained directly on labels assigned to fundus camera images.

Figure 1B:
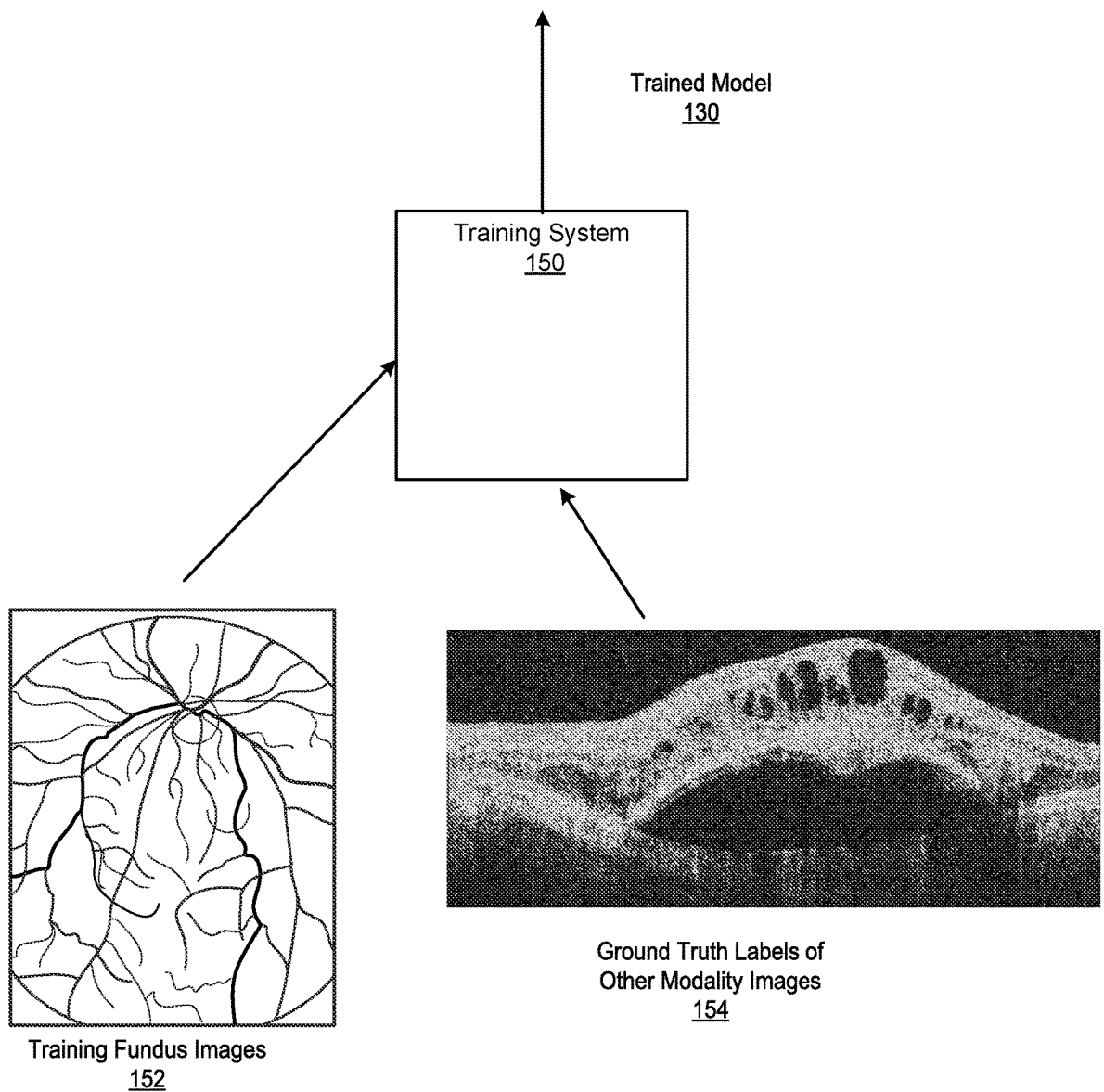
FIG. 1B shows an example training system.

FIG. 1B shows the example training system 150. The training system 150 is an example of a system implemented as computer programs on one or more computers in one or more locations, in which the systems, components, and techniques described below can be implemented.

The training system 150 generates training data for training the machine learning model 130 and then uses the generated training data to train the model 130, i.e., to generate a trained machine learning model 130.

As described above, the training data includes multiple sets of one or more training fundus images and a respective ground truth label for each set of training fundus images. Each set of images includes the same number and same kind of images as the model as configured to receive when making a prediction.

To generate the training data, the system receives a plurality of sets of one or more training fundus images 152 that were captured using a fundus camera. Each set includes one or more images of a corresponding patient's eye.

The system also obtains, for each of the plurality of sets, a ground truth label 154 that has been assigned to a different image of the corresponding patient's eye and, in particular, of the retina (and optionally surrounding tissue) of the corresponding patient's eye. The different image of the corresponding patient's eye is captured by a different modality, i.e., not by a fundus camera.

Generally, the other modality is a modality that is one or more of: (i) more expensive than a typical fundus camera, (ii) has a more complicated workflow to operate than a typical fundus camera (iii) less readily available at testing locations that a typical fundus camera, or (iv) more harmful to the patient than taking a fundus image with a fundus camera.

In other words, images captured by the other imaging modality are generally more informative to an expert operator, e.g., a physician or other clinician, but have one or more downsides that prevent the other imaging modality from being as widely used as a fundus camera.

As one example, the other imaging modality can be an imaging modality that captures three-dimensional images, i.e., as opposed to the two-dimensional images captured by the fundus camera. In particular, these imaging modality can capture a cross-section of the retina of the patient's eye. An example of such an imaging modality is OCT. While an OCT image (also referred to as an OCT exam) or other three-dimensional image is generally more informative to a human expert than a fundus camera image because it depicts the fundus as a three-dimensional volume, OCT imaging devices are more expensive to purchase and maintain and have a much more complicated workflow than a typical fundus camera (i.e., may require a specially-trained expert operator). Thus, OCT imaging devices are much less readily available at screening sites for evaluating patient health than are fundus cameras.

As another example, the other imaging modality can be a radiography apparatus, i.e., an X-ray machine, that captures radiographs of the patient's eye. While a radiograph is generally more informative to a human expert than a fundus camera image, X-ray machines are more expensive to purchase and maintain, have a more complicated workflow, and expose the patient to higher levels of radiation, i.e., are potentially more harmful to the patient, than fundus camera images.

As another example, the other imaging modality can be a low-dose computed tomography modality, i.e., a combination of x-ray equipment and a post-processing computer system. While low-dose computed tomography imaging produces cross-section images that are generally more informative to a human expert than a fundus camera image, the associated machinery is more expensive to purchase and maintain, has a more complicated workflow, and exposes the patient to higher levels of radiation, i.e., is potentially more harmful to the patient, than fundus cameras.

In some cases, the system receives the ground truth labels, i.e., as generated by a human expert from viewing the corresponding other modality image. For example, the system or another system can provide for presentation on the expert user's computer a user interface that allows the user to generate a ground truth label while viewing another modality image.

In some other cases, the system receives the other modality image and processes it using another modality machine learning model that is configured to generate predicted labels of the same type as the fundus image processing machine learning model, but by processing the other modality images instead of fundus camera image.

In either case, the ground truth labels are generated based on the other modality images and therefore take advantage of the additional information that is available from these images that is not available (to human experts) in the fundus camera images.

The system 150 then generates, for each set of one or more training fundus images, a training example that includes (i) the set of one or more training fundus images in association with (ii) the ground truth label assigned to the different image of the retina of the eye of the patient corresponding to the set that has been captured using the different imaging modality. In some cases, as part of generating the training example, the system can pre-process the one or more training fundus images as described below with reference to FIG. 2A.

Once the training data has been generated, the training system 150 trains the model 130 on the training data using supervised learning techniques to generate, by processing the sets of one or more training fundus images, predicted labels that match the ground truth labels associated with the sets. This is accomplished by using the supervised learning techniques to determine trained values of the model parameters from initial, e.g., randomly initialized or initialized according to another machine learning parameter initialization technique, values of the model parameters. For example, if the model 130 is a feedforward neural network, the system 150 can train the model to minimize a loss function using stochastic gradient descent with backpropagation. As another example, if the model 130 is a recurrent neural network, the system 150 can train the model to minimize the loss function using backpropagation through time or truncated backpropagation through time. The loss function can be, e.g., a maximum likelihood loss or a cross-entropy loss, relative to the ground truth label.

The training system 150 then provides the trained values of the model parameters to an inference system for use in predicting labels for new patients or, if the training system 150 is on the same set of computers as the inference system, uses the trained model to predict labels for the new patients.

Figure 2A:
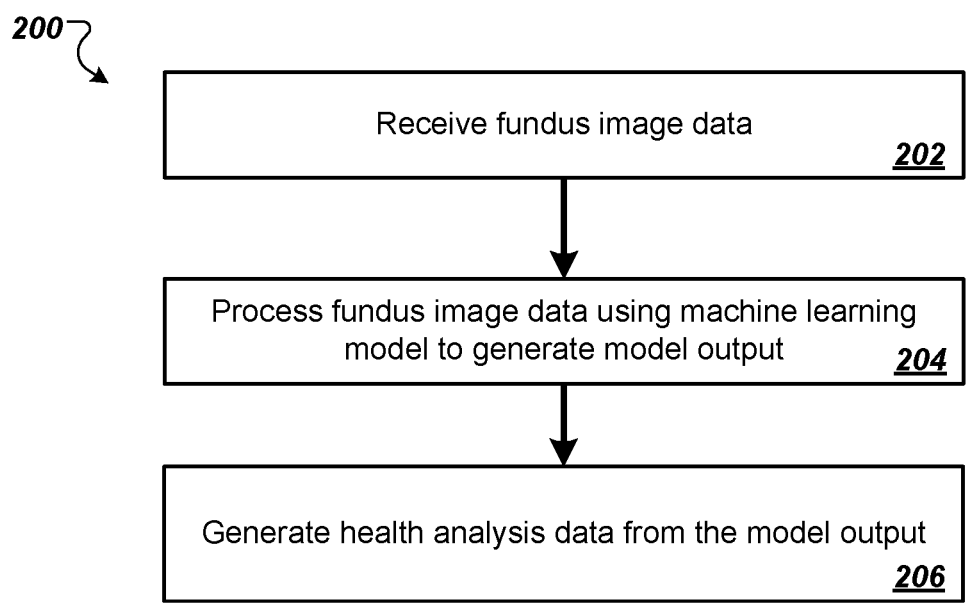
FIG. 2A is a flow diagram of an example process for generating health analysis data.

FIG. 2A is a flow diagram of an example process 200 for generating health analysis data. For convenience, the process 200 will be described as being performed by a system of one or more computers located in one or more locations. For example, a fundus image analysis system, e.g., the fundus image analysis system 100 of FIG. 1, appropriately programmed, can perform the process 200.

The system receives input fundus image data and, optionally, other patient data (step 202).

Generally, the fundus image data includes one or more fundus images of a patient's eye.

In some implementations, the fundus image data includes a single fundus image, e.g., an image that captures the current state of the patient's fundus.

In some other implementations, the fundus image data includes multiple fundus images that capture the current state of the patient's fundus. For example, the fundus image data can include one or more images of the fundus in the patient's left eye and one or more images of the fundus in the patient's right eye. As another example, the fundus images may include multiple different types of fundus photographs. For example, the fundus images may include two or more of: a color fundus photograph, a stereoscopic fundus photograph, a wide field or ultra wide field fundus photograph, or a scanning laser ophthalmoscopy (SLO) fundus photograph. As yet another example, the fundus images can include multiple images captured using different imaging technology, e.g., optical coherence tomography (OCT) and Heidelberg retinal tomography (HRT).

In yet other implementations, the fundus image data includes a temporal sequence of fundus images that capture how the state of the fundus has evolved over time. That is, the temporal sequence includes multiple fundus images, with each fundus image having been taken at a different time. In some implementations, the fundus images are ordered in the temporal sequence from least recent to most recent.

The other patient data is data that characterizes the patient's eye, data that generally characterizes the patient, or both. For example, the other patient data can include ocular measurement data, e.g., eye pressures, visual fields, visual acuity, central corneal thickness, and so on, patient demographics, e.g., age, gender, ethnicity, family history, and so on, or both.

The system processes the input fundus image data and, optionally, the other patient data using a fundus image processing machine learning model to generate a predicted label (step 204). The fundus image processing machine learning model has been trained using the techniques described with reference to FIG. 1B.

Optionally, prior to processing the fundus image data using the machine learning model, the system can pre-process the fundus images. For example, for a given image, the system can apply any of a variety of conventional image processing techniques to the image to improve the quality of the output generated by the machine learning model. As an example, the system may crop, scale, deskew or re-center the image. As another example, the system can remove distortion from the image, e.g., to remove blurring or to re-focus the image, using conventional image processing techniques.

In implementations where the fundus image data includes a single fundus image, the fundus image processing machine learning model is a feedforward machine learning model that has been configured by being trained on appropriately labeled training data to process the fundus image data and, optionally, the other patient data to generate a predicted label that characterizes a particular aspect of the patient's health. For example, the fundus image processing machine learning model may be a deep convolutional neural network. An example of a deep convolutional neural network that can be trained to process a fundus image to generate the predicted labels described in this specification is described in Szegedy, Christian et al. "Going deeper with convolutions." Proceedings of the IEEE Conference on Computer Vision and Pattern Recognition, 2015. Other examples of deep convolutional neural networks, including convolutional neural networks with residual connections, that can be trained to process a fundus image to generate the predicted labels described in this specification are described in Szegedy, Christian, et al. "Inception-v4, Inception-ResNet and the Impact of Residual Connections on Learning," available at http://arxiv.org/abs/1602.07261.

In implementations where the fundus image data includes multiple fundus images that characterize the current state of the patient's fundus, the fundus image processing machine learning model may be a feedforward fundus image processing machine learning model that has been configured by being trained on appropriately labeled training data to process all of the fundus images to generate a predicted label that characterizes a particular aspect of the patient's health. For example, the fundus image processing machine learning model may be a deep convolutional neural network that includes multiple towers of convolutional layers. An example of a deep convolutional neural network that can be trained to process multiple fundus images to generate the predicted labels described in this specification is described in Yue-Hei Ng, Joe, et al. "Beyond short snippets: Deep networks for video classification," Proceedings of the IEEE Conference on Computer Vision and Pattern Recognition, 2015.

In implementations where the fundus image data includes a temporal sequence of fundus images, the fundus image processing machine learning model may be a recurrent fundus image processing machine learning model that has been configured to process each image in the temporal sequence one by one to, for each image, update the internal state of the recurrent fundus image processing machine learning model, and to, after the last image in the temporal sequence has been processed, generate a predicted label that characterizes a particular aspect of the patient's health. For example, the fundus image processing machine learning model may be a recurrent neural network that includes one or more long short-term memory (LSTM) layers. A recurrent neural network that can be trained to process a sequence of fundus images to generate the predicted labels described in this specification is described in Venugopalan, Subhashini, et al. "Sequence to sequence-video to text." Proceedings of the IEEE International Conference on Computer Vision, 2015.

In some implementations, the predicted label is specific to a particular medical condition. Predicted labels that are specific to a particular medical condition are described in more detail below with reference to FIGS. 3-6.

In some other implementations, the predicted label is a prediction of a future state of the fundus of the patient's eye. A predicted label that is a prediction of the future state of a fundus is described in more detail below with reference to FIG. 7.

In yet other implementations, the predicted label is a prediction of the risk of a particular health event occurring in the future. A predicted label that is a prediction of the risk of a particular event occurring is described in more detail below with reference to FIG. 8.

In yet other implementations, the predicted label characterizes the overall health of the patient. A predicted label that characterizes the overall health of the patient is described in more detail below with reference to FIG. 9.

In yet other implementations, the predicted label is a prediction of values of factors that contribute to a particular kind of health-related risk. A predicted label that is a prediction of values of risk factors is described in more detail below with reference to FIG. 10.

The system generates health analysis data from the predicted label (step 206). Generally, the health analysis data characterizes the predicted label in a way that can be presented to a user of the system.

In some implementations, the health analysis data also includes data derived from an intermediate output of the machine learning model that explains the portions of the fundus image or images that the machine learning model focused on when generating the predicted label. In particular, in some implementations, the machine learning model includes an attention mechanism that assigns respective attention weights to each of multiple regions of an input fundus image and then attends to features extracted from those regions in accordance with the attention weights. In these implementations, the system can generate data that identifies the attention weights and include the generated data as part of the health analysis data. For example, the generated data can be an attention map of the fundus image that reflects the attention weights assigned to the regions of the image. For example, the attention map can be overlaid over the fundus image to identify the areas of the patient's fundus that the machine learning model focused on when generating the predicted label. Generating data that identifies areas of the fundus that were focused on by the machine learning model is described in more detail below with reference to FIG. 11.

The system can then provide the health analysis data for presentation to the user in a user interface, e.g., on a user computer of the patient or on a computer of a medical professional, or store the health analysis data for future use.

Figure 2B:
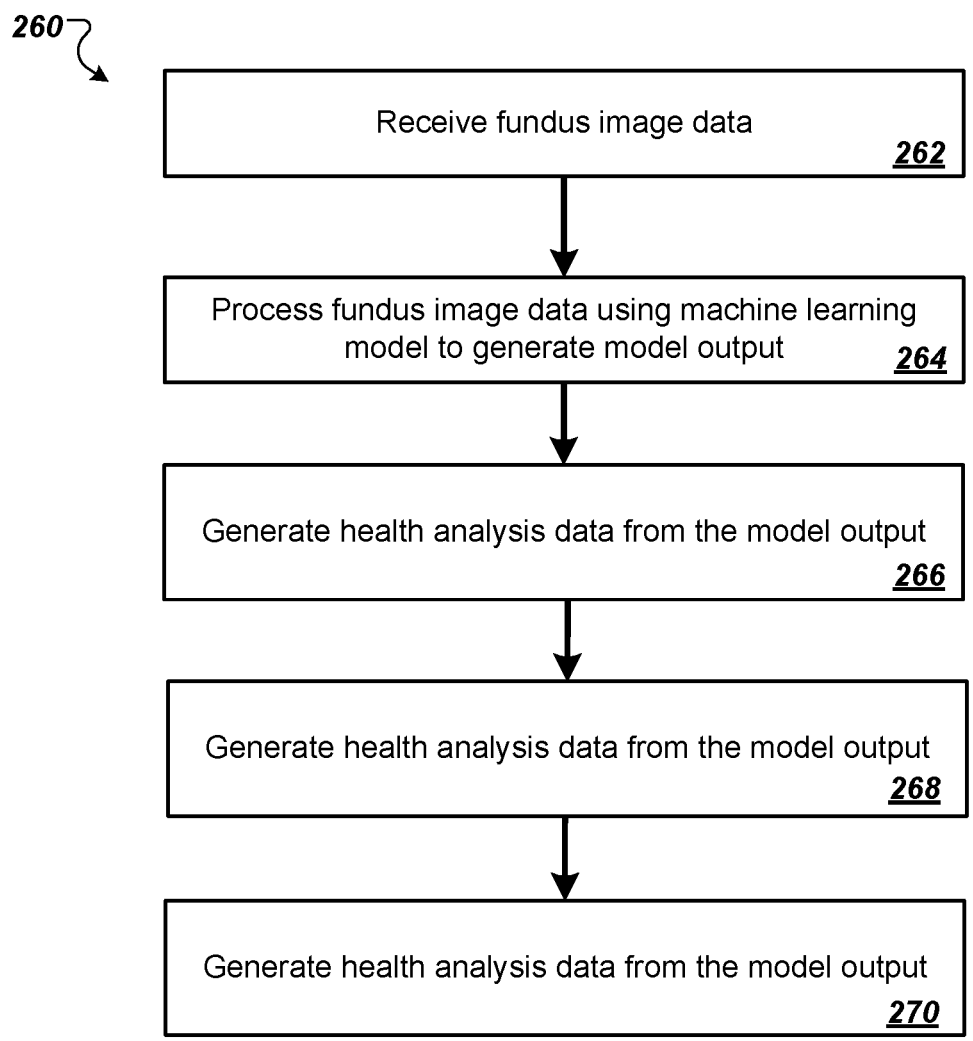
FIG. 2B is a flow diagram of an example process for training the fundus image processing machine learning model.

FIG. 2B is a flow diagram of an example process 260 for training the fundus image processing machine learning model. For convenience, the process 260 will be described as being performed by a system of one or more computers located in one or more locations. For example, a training system, e.g., the training system 100 of FIG. 1, appropriately programmed, can perform the process 260.

The system receives a plurality of sets of one or more training fundus images captured by a fundus camera (step 262). Each set of fundus images corresponds to a respective patient, i.e., all of the images within a given set are of the same patient, and each training fundus image in the set is an image of an eye of the patient corresponding to the set.

The system receives, for each of the plurality of sets, a ground truth label (step 264). Advantageously, the ground truth label is a ground truth label that has been assigned to a different image of the eye of the patient corresponding to the set that has been captured using an imaging modality that is different from the fundus camera. For example the label may have been assigned by a human rater or by a differently trained machine learning model as described above.

The system generates, for each set of one or more training fundus images, a training example that includes (i) the set of one or more training fundus images in association with (ii) the ground truth label assigned to the different image of the eye of the patient corresponding to the set that has been captured using the different imaging modality (step 266).

The system trains the fundus image processing machine learning model on the training examples in the training data to generate, by processing the sets of one or more training fundus images, predicted labels that match the ground truth labels associated with the sets (step 268). In other words, the system adjusts the values of the model parameters to minimize a loss function using a machine learning training technique.

The system provides data specifying the trained fundus image processing machine learning model for use in generating predicted labels for new fundus images (step 270). That is, the system can provide trained model parameter values and, optionally, other data specifying the architecture of the trained machine learning model. The system can provide the data to another system, i.e., an inference system, in order to allow the other system to deploy the trained model for use in generating predicted labels. Alternatively or in addition, the system can use the trained model to generate predicted labels using the provided data without needing to transmit the data to an external system.

Figure 2C:
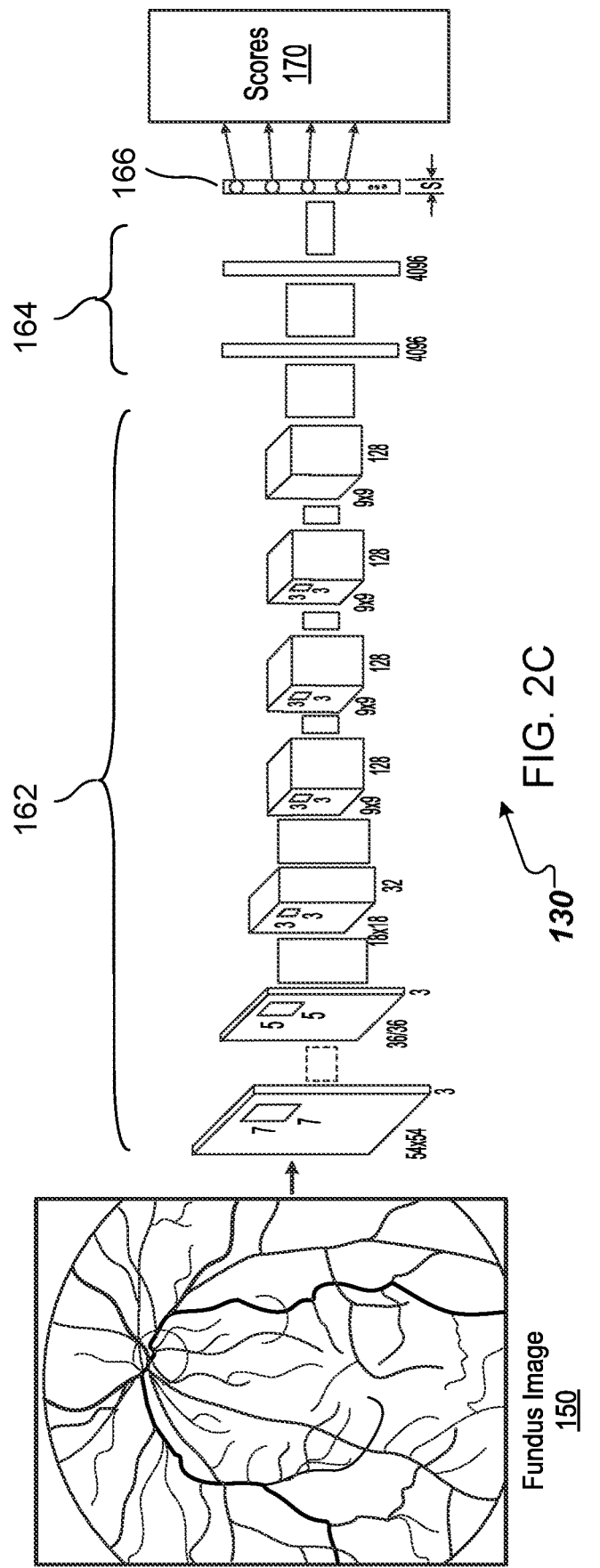
FIG. 2C shows the processing of an example fundus image by the fundus image processing machine learning model.

FIG. 2C shows the processing of an example fundus image 250 by the fundus image processing machine learning model 130. In particular, in the example of FIG. 1B, the fundus image processing machine learning model 130 is a deep convolutional neural network that is configured to receive the fundus image 250 and to process the fundus image 250 to generate a predicted label that characterizes a particular aspect of the patient's health. The fundus image processing machine learning model 130 has been trained using the techniques described above with reference to FIG. 1B.

The convolutional neural network illustrated in FIG. 2C is a simplified example of a deep convolutional neural network and includes a set of convolutional neural network layers 162, followed by a set of fully connected layers 164, and an output layer 166. It will be understood that, in practice, a deep convolutional neural network may include other types of neural network layers, e.g., pooling layers, normalization layers, and so on, and may be arranged in various configurations, e.g., as multiple modules, multiple subnetworks, and so on.

During the processing of the fundus image 250 by the convolutional neural network, the output layer 166 receives an output generated by the last fully connected layer in the set of fully connected layers 164 and generates the predicted label for the fundus image 150. In the example of FIG. 2C, the predicted label is a set of scores 170, with each score being generated by a corresponding node in the output layer 166. As will be described in more detail below, in some cases, the set of scores 170 are specific to particular medical condition. In some other cases, the each score in the set of scores 170 is a prediction of the risk of a respective health event occurring in the future. In yet other cases, the scores in the set of scores 170 characterize the overall health of the patient.

Once the set of scores 170 have been generated, the fundus image analysis system generates patient health analysis data that characterizes an aspect of the patient's health from the scores 170 and provides the health analysis data for presentation to the user in a user interface, e.g., on a user computer of the patient or on a computer of a medical professional, stores the health analysis data for future use, or provides the health analysis data for use for some other immediate purpose.

Figure 3:
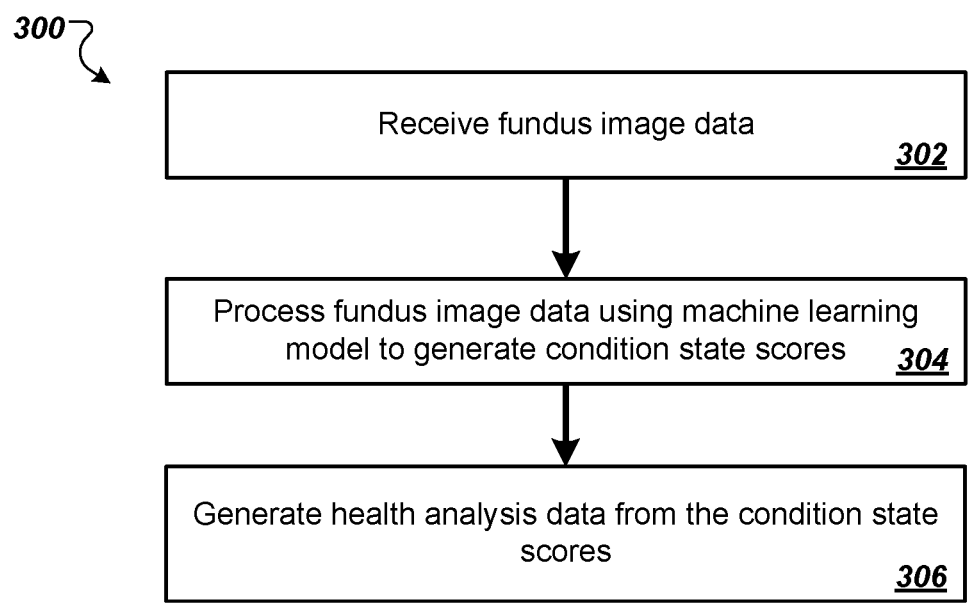
FIG. 3 is a flow diagram of an example process for generating health analysis data that is specific to a particular medical condition.

FIG. 3 is a flow diagram of an example process 300 for generating health analysis data that is specific to a particular medical condition. For convenience, the process 300 will be described as being performed by a system of one or more computers located in one or more locations. For example, a fundus image analysis system, e.g., the fundus image analysis system 100 of FIG. 1, appropriately programmed, can perform the process 300.

The system receives input fundus image data and, optionally, other patient data (step 302).

The system processes the input fundus image data and, optionally, the other patient data using a fundus image processing machine learning model to generate a set of condition state scores (step 304).

Generally, the set of condition state scores are specific to a particular medical condition that the system has been configured to analyze.

In some implementations, the medical condition is a particular eye-related condition.

For example, the particular eye-related condition may be diabetic macular edema (DME). DME is an accumulation of fluid in the macula and can result in blindness.

As another example, the particular eye-related condition may be glaucoma. Generally, glaucoma is a condition in which the optic nerve is damaged, which can result in blindness.

As another example, the particular eye-related condition may be age-related macular degeneration. Generally, age-related macular degeneration is a condition in which the macula, an area near the center of the retina, has deteriorated, which may cause partial or total vision loss.

As another example, the particular eye-related condition may be retinal detachment. Generally, retinal detachment is a disorder in which the retina detaches either partially or completely from its underlying layer of support tissue.

As yet another example, the particular eye-related condition may be ocular occlusions. Generally, an ocular occlusion is the blockage or closing of a blood vessel that carries blood to or from some portion of the eye, e.g., to or from the retina.

As another example, the particular eye-related condition may be the presence of a specific kind of fluid in the eye, e.g., subretinal fluid or intraretinal fluid or both.

In some implementations, the model generates separate predictions for multiple different eye-related conditions. That is, the model makes a separate prediction for each of multiple eye-related conditions. In these cases, the training system trains the model in a multi-task fashion and the ground truth labels for each set of training input images include a respective ground truth label for each of the multiple conditions.

In some other implementations, the specific condition is not an eye-related condition but is instead a neurodegenerative condition, e.g., Parkinson's or Alzheimer's, or another condition that can effectively be analyzed using fundus imagery.

In some implementations, the set of condition state scores includes a single score that represents a likelihood that the patient has the medical condition.

As an example, in the case of DME, the single score may represent a likelihood that the patient has DME.

As another example, in the case of glaucoma, the single score may represent a likelihood that the patient has glaucoma.

As another example, in the case of age-related macular degeneration, the single score may represent a likelihood that the patient has age-related macular degeneration.

As another example, in the case of retinal detachment, the single score may represent a likelihood that the patient has retinal detachment.

As another example, in the case of ocular occlusions, the single score may represent a likelihood that the patient has one or more ocular occlusions.

As another example, in the case of neurodegenerative conditions, the single score may represent a likelihood that the patient has the neurodegenerative condition e.g., Parkinson's or Alzheimer's.

In some other implementations, the set of condition state scores includes a respective score for each of multiple possible levels of the medical condition, with each condition score representing a likelihood that the corresponding level is current level of the condition for the patient.

For example, in the case of DME, the set of scores may include a score for no DME, mild or early-stage DME, moderate-stage DME, severe-stage DME, and, optionally, an indeterminate or unspecified stage.

As another example, in the case of glaucoma, the set of scores may include a score for no glaucoma, mild or early-stage glaucoma, moderate-stage glaucoma, severe-stage glaucoma, and, optionally, an indeterminate or unspecified stage.

As another example, in the case of age-related macular degeneration, the set of scores may include a score for no macular degeneration, early-stage macular degeneration, intermediate macular degeneration, advanced macular degeneration, and, optionally, an indeterminate or unspecified stage.

As another example, in the case of retinal detachment, the set of scores may include a score for no retinal detachment, initial retinal detachment, i.e., only retinal tears or retinal breaks, advanced retinal detachment, and, optionally, an indeterminate or unspecified stage.

As another example, in the case of ocular occlusions, the set of scores may include a score for no ocular occlusions, minor ocular occlusions, severe ocular occlusions, and, optionally, an indeterminate or unspecified stage.

As another example, in the case of neurodegenerative conditions, the set of scores may include a score for not having the neurodegenerative condition, a score for each of multiple stages of the neurodegenerative condition, and, optionally, an indeterminate or unspecified stage.

The system generates health analysis data from the condition state scores (step 306). For example, the system can generate health analysis data that identifies the likelihood that the patient has the medical condition or identifies one or more condition levels that have the highest condition state scores.

Figure 4:
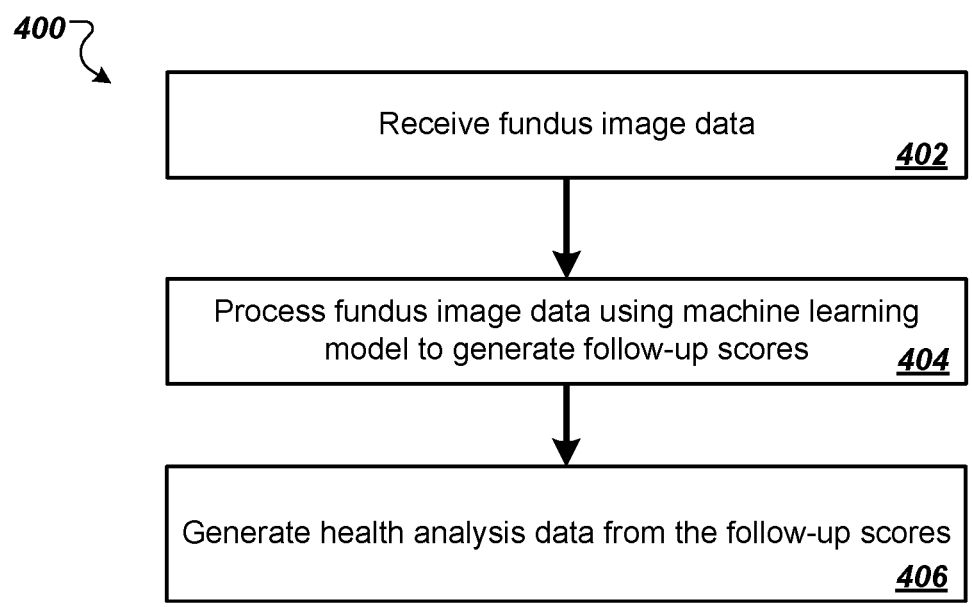
FIG. 4 is a flow diagram of an example process for generating health analysis data that identifies patient follow-up actions.

FIG. 4 is a flow diagram of an example process 400 for generating health analysis data that identifies patient follow-up actions. For convenience, the process 400 will be described as being performed by a system of one or more computers located in one or more locations. For example, a fundus image analysis system, e.g., the fundus image analysis system 100 of FIG. 1, appropriately programmed, can perform the process 400.

The system receives input fundus image data and, optionally, other patient data (step 402).

The system processes the input fundus image data and, optionally, the other patient data using a fundus image processing machine learning model to generate a set of follow-up scores (step 404). The model has been trained as described above with reference to FIG. 1B.

The set of follow-up scores includes a respective score for each of multiple possible follow-up actions that can be taken by the patient to treat a particular medical condition. For example, the set of possible follow-up actions may include performing a re-screening at a future time, visiting a doctor at a future time, and visiting a doctor immediately. Each follow-up score represents a likelihood that the corresponding follow-up action is the proper action to be taken to effectively treat the medical condition.

The system generates health analysis data from the follow-up scores (step 406). For example, the system can generate health analysis data that recommends that the patient take the follow-up action that has the highest follow-up score.

Figure 5:
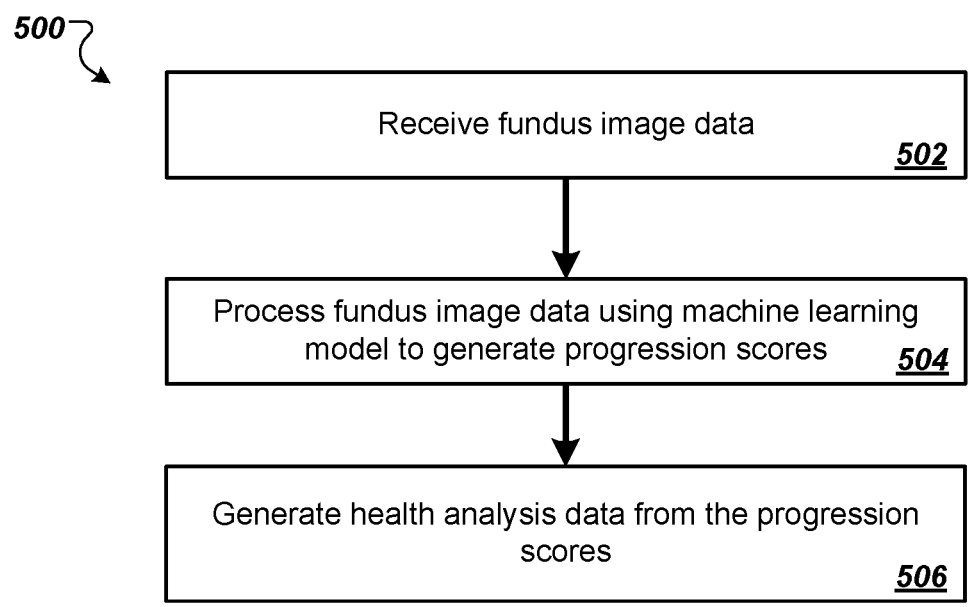
FIG. 5 is a flow diagram of an example process for generating health analysis data that predicts the likely progression of a medical condition.

FIG. 5 is a flow diagram of an example process 500 for generating health analysis data that predicts the likely progression of a medical condition. For convenience, the process 500 will be described as being performed by a system of one or more computers located in one or more locations. For example, a fundus image analysis system, e.g., the fundus image analysis system 100 of FIG. 1, appropriately programmed, can perform the process 500.

The system receives input fundus image data and, optionally, other patient data (step 502).

The system processes the input fundus image data and, optionally, the other patient data using a fundus image processing machine learning model to generate a set of progression scores (step 504). The set of progression scores are specific to a particular medical condition that the system has been configured to analyze. The set of condition state scores includes a respective score for each of multiple possible levels of the medical condition, with each condition score representing a likelihood that the corresponding level will be the level of the condition for the patient at a predetermined future time, e.g., in 6 months, in 1 year, or in 5 years.

For example, in the case of glaucoma, the set of scores may include a score for no glaucoma, mild or early-stage glaucoma, moderate-stage glaucoma, and severe-stage glaucoma, with the score for each stage representing the likelihood that the corresponding stage will be the stage of glaucoma for the patient at the future time.

As another example, in the case of age-related macular degeneration, the set of scores may include a score for no macular degeneration, early-stage macular degeneration, intermediate-stage macular degeneration, and advanced-stage macular degeneration, and, optionally, with the score for each stage representing the likelihood that the corresponding stage will be the stage of macular degeneration for the patient at the future time.

As another example, in the case of neurodegenerative conditions, the set of scores may include a score for not having the neurodegenerative condition and a score for each of multiple stages of the neurodegenerative condition, with the score for each stage representing the likelihood that the corresponding stage will be the stage of the condition for the patient at the future time.

The system generates health analysis data from the progression scores (step 506). The health analysis data identifies the likely progression of the medical condition for the patient. For example, the system can generate health analysis data that identifies one or more of the possible condition levels and, for each possible condition level, the likelihood that the corresponding level will be the future level of the condition for the patient.

Figure 6:
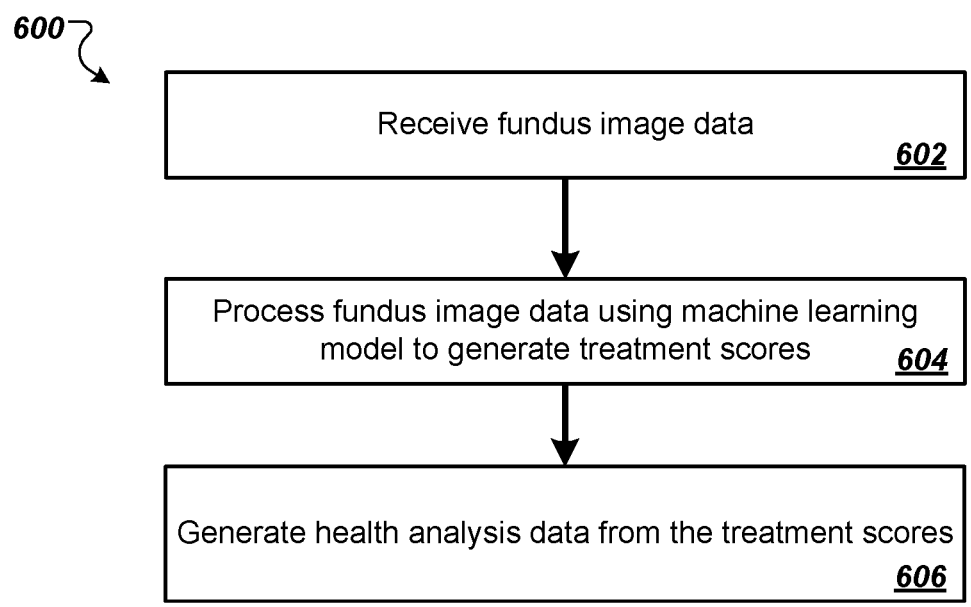
FIG. 6 is a flow diagram of an example process for generating health analysis data that predicts the proper treatment for a medical condition for a given patient.

FIG. 6 is a flow diagram of an example process 600 for generating health analysis data that predicts the proper treatment for a medical condition for a given patient. For convenience, the process 600 will be described as being performed by a system of one or more computers located in one or more locations. For example, a fundus image analysis system, e.g., the fundus image analysis system 100 of FIG. 1, appropriately programmed, can perform the process 600.

The system receives input fundus image data and, optionally, other patient data (step 602).

The system processes the input fundus image data and, optionally, the other patient data using a fundus image processing machine learning model to generate a set of treatment scores (step 604).

The set of treatment scores include a respective score for each of multiple possible treatments for a given medical condition, with each treatment score representing a likelihood that the corresponding treatment is the most effective treatment for the condition for the current patient.

For example, the set of treatment scores can include a respective score for each of multiple medications that can be prescribed to a patient that has the medical condition.

As another example, the set of treatment scores can include a respective score for each of multiple treatment plans for a given medical condition, e.g., a respective score for one or more medical procedures and a score for rehabilitation without undergoing a procedure.

The system generates health analysis data from the progression scores (step 606). For example, the health analysis data can identify one or more of the highest-scoring treatments.

Figure 7:
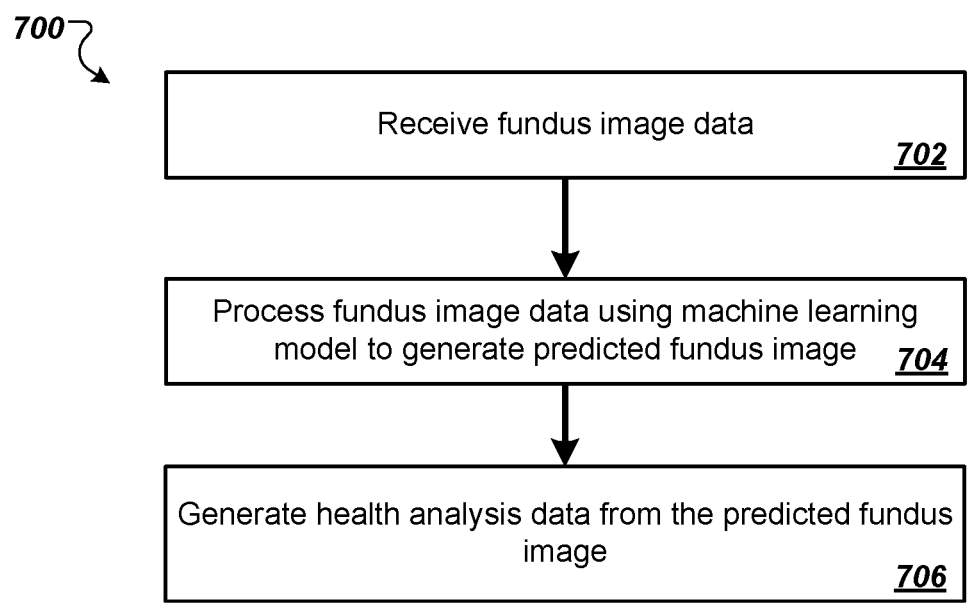
FIG. 7 is a flow diagram of an example process for generating health analysis data that includes a predicted fundus image.

FIG. 7 is a flow diagram of an example process 700 for generating health analysis data that includes a predicted fundus image. For convenience, the process 700 will be described as being performed by a system of one or more computers located in one or more locations. For example, a fundus image analysis system, e.g., the fundus image analysis system 100 of FIG. 1, appropriately programmed, can perform the process 700.

The system receives input fundus image data and, optionally, other patient data (step 702).

The system processes the input fundus image data and, optionally, the other patient data using a fundus image processing machine learning model to generate a predicted fundus image (step 704).

The predicted fundus image is an image of the fundus of the eye of the patient as it is predicted to look at a particular future time, e.g., in six months, in one year, or in five years.

For example, the fundus image processing machine learning model may be a convolutional neural network that is configured through training to predict, for each pixel in the input fundus image, the color of the pixel at the particular future time.

As another example, when the fundus image data includes a temporal sequence of fundus images, the fundus image processing machine learning model may be a recurrent neural network that is configured through training to, for each pixel in the most recent fundus image in the sequence, predict the color of the pixel at the particular future time. The system can use the predicted color values for the pixels to generate the predicted fundus image.

The system generates health analysis data from the progression scores (step 706). For example, the health analysis data can include the predicted fundus image and, optionally, additional health analysis data.

Figure 8:
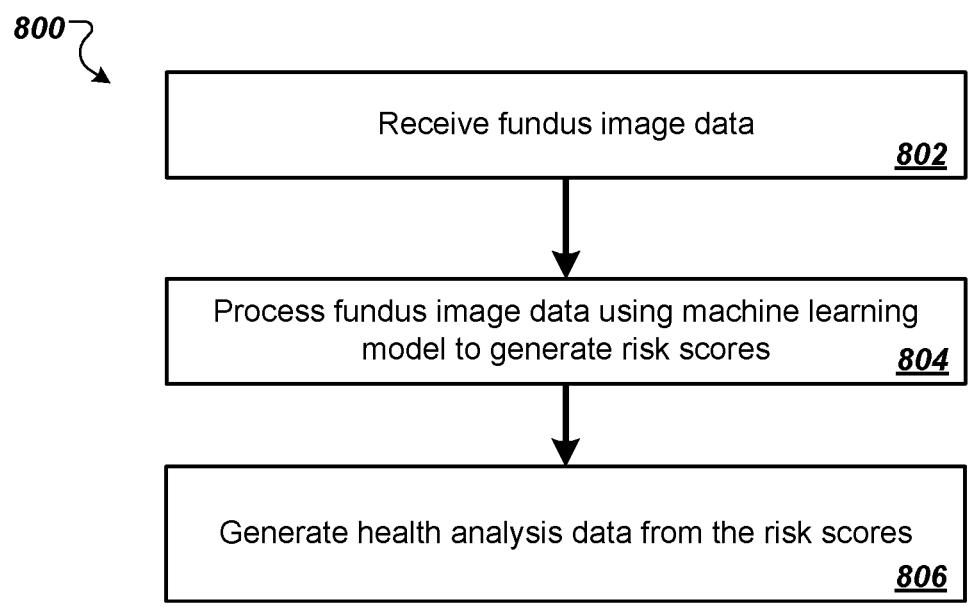
FIG. 8 is a flow diagram of an example process for generating health analysis data that predicts the risk of a health event occurring.

FIG. 8 is a flow diagram of an example process 800 for generating health analysis data that predicts the risk of a health event occurring. For convenience, the process 800 will be described as being performed by a system of one or more computers located in one or more locations. For example, a fundus image analysis system, e.g., the fundus image analysis system 100 of FIG. 1, appropriately programmed, can perform the process 800.

The system receives input fundus image data and, optionally, other patient data (step 802).

The system processes the input fundus image data and, optionally, the other patient data using a fundus image processing machine learning model to generate a set of risk scores (step 804).

In some implementations, the set of risk scores includes a single score that measures a particular kind of risk. For example, the score may measure a predicted cardiovascular risk of the patient, e.g., may be a predicted Framingham risk score that measures the 10-year cardiovascular risk of the patient.

In some other implementations, the set of risk scores may be specific to a particular undesirable health event.

For example, the undesirable health event may be a heart attack, a stroke, mortality, hospitalization, a fall, complications pre-operation or post-operation, and so on. In some of these implementations, the set of risk scores includes a single score that represents a likelihood of the undesirable health event occurring in the future, e.g., within a specified future time window. In others of these implementations, the set of risk scores includes a respective score for each of multiple risk levels, e.g., low, medium, and high, for the health event, with each risk score representing a likelihood that the corresponding risk level is the current risk level of the health event occurring.

In yet other implementations, the set of scores can include multiple scores, with each score corresponding to a respective undesirable health event and representing a likelihood that the corresponding undesirable health event will occur in the future, e.g., within a specified future time window.

The system generates health analysis data from the risk scores (step 806). For example, in implementations where the set of scores includes a single score, the health analysis data can identify the single score. As another example, where the set of scores includes multiple scores, the health analysis data can identify the highest-scoring risk level.

Figure 9:
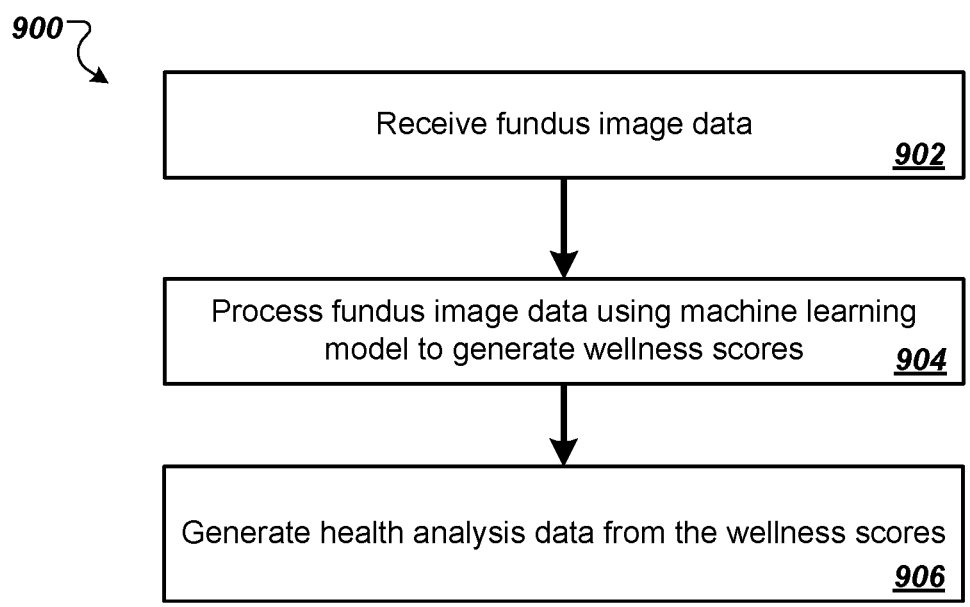
FIG. 9 is a flow diagram of an example process for generating health analysis data that characterizes the overall health of the patient.

FIG. 9 is a flow diagram of an example process 900 for generating health analysis data that characterizes the overall health of the patient. For convenience, the process 900 will be described as being performed by a system of one or more computers located in one or more locations. For example, a fundus image analysis system, e.g., the fundus image analysis system 100 of FIG. 1, appropriately programmed, can perform the process 900.

The system receives input fundus image data and, optionally, other patient data (step 902).

The system processes the input fundus image data and, optionally, the other patient data using a fundus image processing machine learning model to generate a set of wellness scores (step 904).

In some implementations, the set of wellness scores includes a single score that measures the overall health of the patient on a predetermined scale.

In some other implementations, the set of wellness scores may include a respective score for each of multiple wellness labels that each characterize the overall health of the patient. For example, the wellness labels may be "very healthy," "healthy," "somewhat unhealthy," and "very unhealthy." Each score represents a likelihood that the corresponding wellness label accurately characterizes the current health of the patient. Thus, for example the score for the wellness label "very healthy" represents the likelihood that the patient is very healthy, while the score for the "somewhat unhealthy" label represents the likelihood that the patient is somewhat unhealthy.

The system generates health analysis data from the risk scores (step 906). For example, in implementations where the set of scores includes a single score, the health analysis data can identify the single score. As another example, where the set of scores includes multiple scores, the health analysis data can identify the highest-scoring wellness label.

Figure 10:
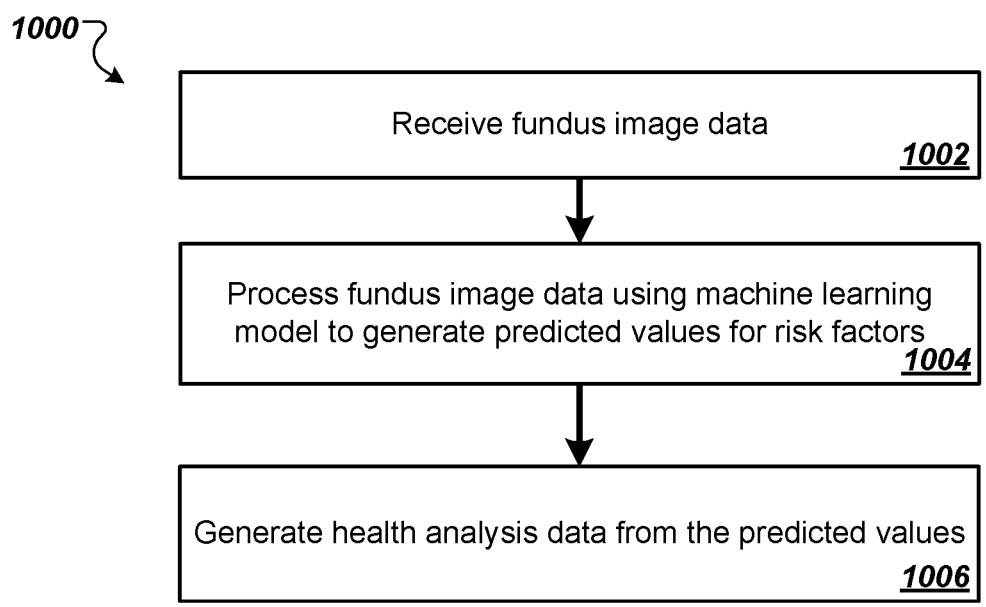
FIG. 10 is a flow diagram of an example process for generating health analysis data that includes predicted values for one or more risk factors.

FIG. 10 is a flow diagram of an example process 1000 for generating health analysis data that includes predicted values for one or more risk factors. For convenience, the process 1000 will be described as being performed by a system of one or more computers located in one or more locations. For example, a fundus image analysis system, e.g., the fundus image analysis system 100 of FIG. 1, appropriately programmed, can perform the process 1000.

The system receives input fundus image data that includes one or more fundus images (step 1002).

The system processes the input fundus image data using a fundus image processing machine learning model to generate a respective predicted value for each of one or more risk factors (step 1004).

Each of the risk factors is a factor that contributes to the risk of one of a particular set of health-related events happening to the patient. For example, when the risk is cardiovascular risk, the particular set of health-related events can be a health event that is classified as a major cardiovascular health event, e.g., myocardial infarction, heart failure, percutaneous cardiac intervention, coronary artery bypass grafting, malignant dysrhythmia, cardiac shock, implantable cardiac defibrillator, malignant dysrhythmia, cardiac-related mortality, and so on.

Continuing the example of cardiovascular risk, the risk factors can include one or more of: age, gender, body mass index, systolic blood pressure, diastolic blood pressure, a measure of HbA1c (glycated hemoglobin), or smoking status, i.e., whether or not the patient smokes cigarettes.

In some implementations, the system employs multiple machine learning models that each generate a predicted value for a different subset of the risk factors. For example, one model may generate predicted values for binary risk factors that can only take one of two values, e.g., smoking status and gender, while another model may generate predicted values for continuous risk factors that can take continuous values from some value range, e.g., age, body mass index, and blood pressure. Each of the two models may have similar architectures, but with different parameter values.

The system generates health analysis data from the predicted values (step 1006). For example, the health analysis data can identify each generated predicted value. In some cases, the system can use the predicted values to compute a measure of the particular risk and provide the computed measure of risk as part of the health analysis data. For example, the system can provide the predicted values as input to another machine learning model configured to predict the measure of risk or to a hard-coded formula to obtain the computed measure. For example, in the case of cardiovascular risk, the system can compute a Framingham risk score using the predicted values. Alternatively, the system can provide the predicted values as input to a machine learning model that has been trained to predict a risk measure based on values of risk factors.

Figure 11:
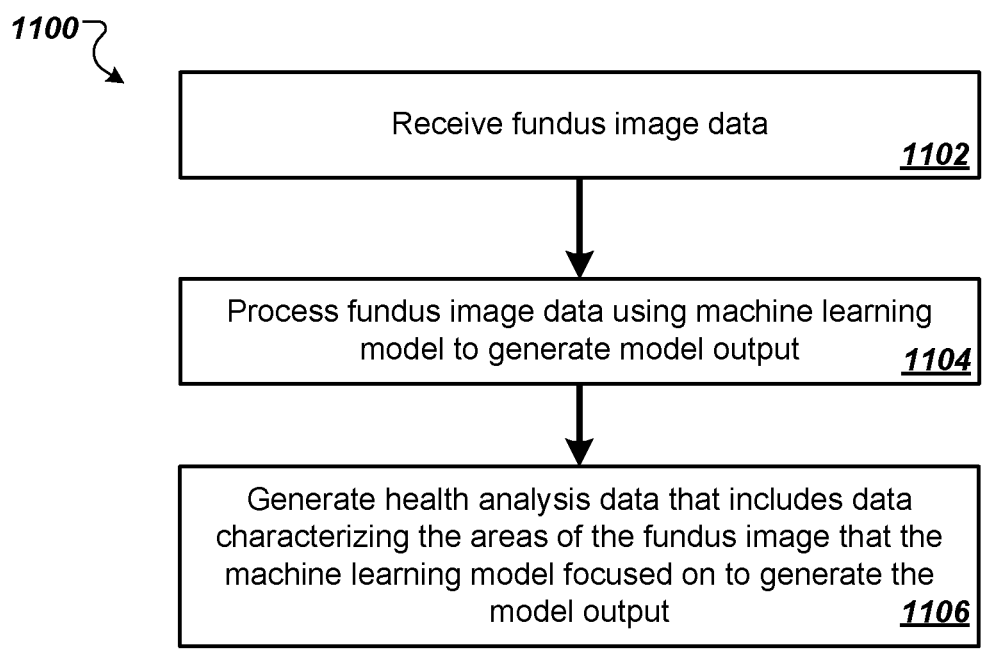
FIG. 11 is a flow diagram of an example process for generating health analysis data that includes data identifying locations in a fundus image that were focused on by the machine learning model when generating the predicted label.

FIG. 11 is a flow diagram of an example process 1100 for generating health analysis data that includes data identifying locations in a fundus image that were focused on by the machine learning model when generating the predicted label. For convenience, the process 1100 will be described as being performed by a system of one or more computers located in one or more locations. For example, a fundus image analysis system, e.g., the fundus image analysis system 100 of FIG. 1, appropriately programmed, can perform the process 1100.

The system receives input fundus image data and, optionally, other patient data (step 1102).

The system processes the input fundus image data and, optionally, the other patient data using a fundus image processing machine learning model to generate a predicted label (step 1104). The predicted label can be any of the predicted labels described above with reference to FIGS. 2-10.

In particular, the machine learning model may be a model that includes one or more initial convolutional layers followed by an attention mechanism, which in turn is followed by one or more additional neural network layers.

The initial convolutional layers process each fundus image in the fundus image data to extract a respective feature vector for each of multiple regions in the fundus image.

The attention mechanism determines an attention weight for each of the regions in the fundus image and then attends to the feature vectors in accordance with the corresponding attention weights to generate an attention output. Generally, the attention mechanism attends to the feature vectors by computing a weighted sum or a weighted mean of the feature vectors, with the weight for each feature vector being the attention weight for the corresponding region. To determine the attention weights, the system can use any of a variety of attention schemes to determine the relevance of each of the feature vectors to generate the predicted label for the fundus image and then normalize the determined relevances to compute the attention weights. Example attention schemes include processing the feature vectors using one or more fully-connected layers to determine the relevance and determining the relevance of a given feature vector by computing a cosine similarity between the feature vector and a learned context vector. An example attention mechanism that can be adapted for use in the fundus image processing machine learning model is described in "Show, Attend and Tell: Neural Image Caption Generation with Visual Attention," Xu et al, available at https://arxiv.org/abs/1502.03044.

The additional neural network layers that follow the attention mechanism receive the attention output(s) for each of the fundus images and generate the predicted label from the attention output. For example, when the machine learning model is a recurrent neural network, the additional neural network layers include one or more recurrent layers. When the machine learning model is a convolutional neural network, the additional neural network layers can include convolutional neural network layers, fully-connected layers or other conventional feedforward neural network layers.

The system generates health analysis data from the risk scores (step 1106). In particular, as described above, the health analysis data characterizes the predicted label in a way that can be presented to a user of the system.

In addition, the health analysis data includes data characterizing the areas of the fundus image that the machine learning model focused on to generate the predicted label. In particular, the health analysis data include data identifying the attention weights assigned to the regions in the fundus image. For example, the system can generate an attention map that identifies, for each pixel in the fundus image, the attention weight assigned to the pixel, i.e., the attention weight for the region of the image that the pixel belongs to. For example, the attention map can be a heat map that represents the attention weights as colors. In some implementations, the system provides the attention map as an overlay of the corresponding fundus image.

This specification uses the term "configured" in connection with systems and computer program components. For a system of one or more computers to be configured to perform particular operations or actions means that the system has installed on it software, firmware, hardware, or a combination of them that in operation cause the system to perform the operations or actions. For one or more computer programs to be configured to perform particular operations or actions means that the one or more programs include instructions that, when executed by data processing apparatus, cause the apparatus to perform the operations or actions.

Embodiments of the subject matter and the functional operations described in this specification can be implemented in digital electronic circuitry, in tangibly-embodied computer software or firmware, in computer hardware, including the structures disclosed in this specification and their structural equivalents, or in combinations of one or more of them. Embodiments of the subject matter described in this specification can be implemented as one or more computer programs, i.e., one or more modules of computer program instructions encoded on a tangible non transitory storage medium for execution by, or to control the operation of, data processing apparatus. The computer storage medium can be a machine-readable storage device, a machine-readable storage substrate, a random or serial access memory device, or a combination of one or more of them. Alternatively or in addition, the program instructions can be encoded on an artificially generated propagated signal, e.g., a machine-generated electrical, optical, or electromagnetic signal, that is generated to encode information for transmission to suitable receiver apparatus for execution by a data processing apparatus.

The term "data processing apparatus" refers to data processing hardware and encompasses all kinds of apparatus, devices, and machines for processing data, including by way of example a programmable processor, a computer, or multiple processors or computers. The apparatus can also be, or further include, special purpose logic circuitry, e.g., an FPGA (field programmable gate array) or an ASIC (application specific integrated circuit). The apparatus can optionally include, in addition to hardware, code that creates an execution environment for computer programs, e.g., code that constitutes processor firmware, a protocol stack, a database management system, an operating system, or a combination of one or more of them.

A computer program, which may also be referred to or described as a program, software, a software application, an app, a module, a software module, a script, or code, can be written in any form of programming language, including compiled or interpreted languages, or declarative or procedural languages; and it can be deployed in any form, including as a stand alone program or as a module, component, subroutine, or other unit suitable for use in a computing environment. A program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, sub programs, or portions of code. A computer program can be deployed to be executed on one computer or on multiple computers that are located at one site or distributed across multiple sites and interconnected by a data communication network.

In this specification, the term "database" is used broadly to refer to any collection of data: the data does not need to be structured in any particular way, or structured at all, and it can be stored on storage devices in one or more locations. Thus, for example, the index database can include multiple collections of data, each of which may be organized and accessed differently.

Similarly, in this specification the term "engine" is used broadly to refer to a software-based system, subsystem, or process that is programmed to perform one or more specific functions. Generally, an engine will be implemented as one or more software modules or components, installed on one or more computers in one or more locations. In some cases, one or more computers will be dedicated to a particular engine; in other cases, multiple engines can be installed and running on the same computer or computers.

The processes and logic flows described in this specification can be performed by one or more programmable computers executing one or more computer programs to perform functions by operating on input data and generating output. The processes and logic flows can also be performed by special purpose logic circuitry, e.g., an FPGA or an ASIC, or by a combination of special purpose logic circuitry and one or more programmed computers.

Computers suitable for the execution of a computer program can be based on general or special purpose microprocessors or both, or any other kind of central processing unit. Generally, a central processing unit will receive instructions and data from a read only memory or a random access memory or both. The essential elements of a computer are a central processing unit for performing or executing instructions and one or more memory devices for storing instructions and data. The central processing unit and the memory can be supplemented by, or incorporated in, special purpose logic circuitry. Generally, a computer will also include, or be operatively coupled to receive data from or transfer data to, or both, one or more mass storage devices for storing data, e.g., magnetic, magneto optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device, e.g., a universal serial bus (USB) flash drive, to name just a few.

Computer readable media suitable for storing computer program instructions and data include all forms of non volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks.

To provide for interaction with a user, embodiments of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's device in response to requests received from the web browser. Also, a computer can interact with a user by sending text messages or other forms of message to a personal device, e.g., a smartphone that is running a messaging application, and receiving responsive messages from the user in return.

Data processing apparatus for implementing machine learning models can also include, for example, special-purpose hardware accelerator units for processing common and compute-intensive parts of machine learning training or production, i.e., inference, workloads.

Machine learning models can be implemented and deployed using a machine learning framework, .e.g., a TensorFlow framework, a Microsoft Cognitive Toolkit framework, an Apache Singa framework, or an Apache MXNet framework.

Embodiments of the subject matter described in this specification can be implemented in a computing system that includes a back end component, e.g., as a data server, or that includes a middleware component, e.g., an application server, or that includes a front end component, e.g., a client computer having a graphical user interface, a web browser, or an app through which a user can interact with an implementation of the subject matter described in this specification, or any combination of one or more such back end, middleware, or front end components. The components of the system can be interconnected by any form or medium of digital data communication, e.g., a communication network. Examples of communication networks include a local area network (LAN) and a wide area network (WAN), e.g., the Internet.

The computing system can include clients and servers. A client and server are generally remote from each other and typically interact through a communication network. The relationship of client and server arises by virtue of computer programs running on the respective computers and having a client-server relationship to each other. In some embodiments, a server transmits data, e.g., an HTML page, to a user device, e.g., for purposes of displaying data to and receiving user input from a user interacting with the device, which acts as a client. Data generated at the user device, e.g., a result of the user interaction, can be received at the server from the device.

While this specification contains many specific implementation details, these should not be construed as limitations on the scope of any invention or on the scope of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially be claimed as such, one or more features from a claimed combination can in some cases be excised from the combination, and the claimed combination may be directed to a subcombination or variation of a subcombination.

Similarly, while operations are depicted in the drawings and recited in the claims in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described above should not be understood as requiring such separation in all embodiments, and it should be understood that the described program components and systems can generally be integrated together in a single software product or packaged into multiple software products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In some cases, multitasking and parallel processing may be advantageous.

What is claimed is:

1. A method performed by one or more computers, the method comprising:
   generating training data for training a fundus image processing machine learning model,
      wherein the fundus image processing machine learning model is configured to process one or more fundus images captured by a fundus camera to generate a predicted label,
      wherein each of the one or more fundus images are an image of a fundus of an eye of a patient,
      wherein the predicted label characterizes a health of the patient, and
      wherein generating the training data comprises:
         receiving a plurality of sets of one or more training fundus images captured by a fundus camera, each set corresponding to a respective patient, and each training fundus image in the set being an image of an eye of the patient corresponding to the set;
         receiving, for each of the plurality of sets, a ground truth label assigned to a different image of the eye of the patient corresponding to the set that has been captured using an imaging modality that is different from the fundus camera; and generating, for each set of one or more training fundus images, a training example that includes (i) the set of one or more training fundus images in association with (ii) the ground truth label assigned to the different image of the eye of the patient corresponding to the set that has been captured using the different imaging modality;

training the fundus image processing machine learning model on the training examples in the training data to generate, by processing the sets of one or more training fundus images, predicted labels that match the ground truth labels associated with the sets; and providing data specifying the trained fundus image processing machine learning model for use in generating predicted labels for new fundus images.

2. The method of claim 1, wherein the fundus images captured by the fundus camera are two-dimensional images and wherein the different images captured using the different imaging modality are three-dimensional images.

3. The method of claim 2, wherein the different imaging modality is a modality that captures cross-sections of a retina of the eye.

4. The method of claim 2, wherein the different imaging modality is optical coherence tomography (OCT).

5. The method of claim 1, wherein the predicted labels and the ground truth labels characterize the health of the patient with respect to Diabetic macular edema (DME).

6. The method of claim 5, wherein the predicted labels and the ground truth labels comprise a condition state score that represents a likelihood that the patient has DME.

7. The method of claim 5, wherein the predicted labels and the ground truth labels comprise a plurality of condition state scores, each condition state score corresponding to a respective possible level of DME and each condition state score representing a respective likelihood that the corresponding possible level of DME is a current level of DME for the patient.

8. The method of claim 1, further comprising:
receiving a new fundus image captured by a fundus camera, the new fundus image of an eye of a new patient; and
processing the received new fundus image using the trained fundus image processing machine learning model to generate a predicted label for the new fundus image.

9. A system comprising one or more computers and one or more storage devices storing instructions that when executed by one or more computers cause the one or more computers to perform operations comprising:
generating training data for training a fundus image processing machine learning model,
wherein the fundus image processing machine learning model is configured to process one or more fundus images captured by a fundus camera to generate a predicted label,
wherein each of the one or more fundus images are an image of a fundus of an eye of a patient,
wherein the predicted label characterizes a health of the patient, and
wherein generating the training data comprises:
receiving a plurality of sets of one or more training fundus images captured by a fundus camera, each set corresponding to a respective patient, and each training fundus image in the set being an image of an eye of the patient corresponding to the set;
receiving, for each of the plurality of sets, a ground truth label assigned to a different image of the eye of the patient corresponding to the set that has been captured using an imaging modality that is different from the fundus camera; and
generating, for each set of one or more training fundus images, a training example that includes (i) the set of one or more training fundus images in association with (ii) the ground truth label assigned to the different image of the eye of the patient corresponding to the set that has been captured using the different imaging modality;

training the fundus image processing machine learning model on the training examples in the training data to generate, by processing the sets of one or more training fundus images, predicted labels that match the ground truth labels associated with the sets; and providing data specifying the trained fundus image processing machine learning model for use in generating predicted labels for new fundus images.

10. The system of claim 9, wherein the fundus images captured by the fundus camera are two-dimensional images and wherein the different images captured using the different imaging modality are three-dimensional images.

11. The system of claim 10, wherein the different imaging modality is a modality that captures cross-sections of a retina of the eye.

12. The system of claim 10, wherein the different imaging modality is optical coherence tomography (OCT).

13. The system of claim 9, wherein the predicted labels and the ground truth labels characterize the health of the patient with respect to Diabetic macular edema (DME).

14. The system of claim 13, wherein the predicted labels and the ground truth labels comprise a condition state score that represents a likelihood that the patient has DME.

15. The system of claim 13, wherein the predicted labels and the ground truth labels comprise a plurality of condition state scores, each condition state score corresponding to a respective possible level of DME and each condition state score representing a respective likelihood that the corresponding possible level of DME is a current level of DME for the patient.

16. The system of claim 9, the operations further comprising:
receiving a new fundus image captured by a fundus camera, the new fundus image being an image of an eye of a new patient; and
processing the received new fundus image using the trained fundus image processing machine learning model to generate a predicted label for the new fundus image.

17. One or more non-transitory computer-readable media storing instructions that when executed by one or more computers cause the one or more computers to perform operations comprising:
generating training data for training a fundus image processing machine learning model,
wherein the fundus image processing machine learning model is configured to process one or more fundus images captured by a fundus camera to generate a predicted label,
wherein each of the one or more fundus images are an image of a fundus of an eye of a patient,
wherein the predicted label characterizes a health of the patient, and
wherein generating the training data comprises:
receiving a plurality of sets of one or more training fundus images captured by a fundus camera, each set corresponding to a respective patient, and each training fundus image in the set being an image of an eye of the patient corresponding to the set;

receiving, for each of the plurality of sets, a ground truth label assigned to a different image of the eye of the patient corresponding to the set that has been captured using an imaging modality that is different from the fundus camera; and generating, for each set of one or more training fundus images, a training example that includes (i) the set of one or more training fundus images in association with (ii) the ground truth label assigned to the different image of the eye of the patient corresponding to the set that has been captured using the different imaging modality;

training the fundus image processing machine learning model on the training examples in the training data to generate, by processing the sets of one or more training fundus images, predicted labels that match the ground truth labels associated with the sets; and providing data specifying the trained fundus image processing machine learning model for use in generating predicted labels for new fundus images.

18. The computer-readable storage media of claim 17, wherein the fundus images captured by the fundus camera are two-dimensional images and wherein the different images captured using the different imaging modality are three-dimensional images.

19. The computer-readable storage media of claim 18, wherein the different imaging modality is a modality that captures cross-sections of a retina of the eye.

20. The computer-readable storage media of claim 18, wherein the different imaging modality is optical coherence tomography (OCT).

* * * * *